US011076902B2

(12) United States Patent
Lieberman (10) Patent No.: US 11,076,902 B2
(45) Date of Patent: Aug. 3, 2021

(54) LOCKING SCREW ASSEMBLY FOR FACILITATING DIRECT LATERAL INTERBODY FUSION PROCEDURES

(71) Applicant: Phoenix Spine Holdings, Inc., Phoenix, AZ (US)

(72) Inventor: Daniel Lieberman, Phoenix, AZ (US)

(73) Assignee: Phoenix Spine Holdings, Inc., Phoenix, AZ (US)

( * ) Notice: Subject to any disclaimer, the term of this patent is extended or adjusted under 35 U.S.C. 154(b) by 149 days.

(21) Appl. No.: 15/902,818

(22) Filed: Feb. 22, 2018

(65) Prior Publication Data

US 2019/0254725 A1    Aug. 22, 2019

(51) Int. Cl.
*A61B 17/56* (2006.01)
*A61B 17/86* (2006.01)
*A61B 17/70* (2006.01)
*A61B 17/80* (2006.01)

(52) U.S. Cl.
CPC ....... *A61B 17/8695* (2013.01); *A61B 17/7059* (2013.01); *A61B 17/8085* (2013.01); *A61B 17/8605* (2013.01); *A61B 17/8625* (2013.01); *A61B 17/8645* (2013.01); *A61B 2017/564* (2013.01)

(58) Field of Classification Search
CPC ............ A61B 17/7059; A61B 17/7058; A61B 17/8052; A61B 17/8057; A61B 17/808; A61B 17/1728; A61B 2017/0256
See application file for complete search history.

(56) References Cited

U.S. PATENT DOCUMENTS

| | | |
|---|---|---|
| 2,112,056 A | 3/1938 | Wappler |
| 3,763,843 A | 10/1973 | Fisher et al. |
| 4,239,296 A | 12/1980 | Kaub |
| 4,388,921 A * | 6/1983 | Sutter ............... A61B 17/8047 411/537 |
| 4,576,147 A | 3/1986 | Hashiguchi |
| 4,624,243 A | 11/1986 | Lowery et al. |
| 4,697,577 A | 10/1987 | Forkner |
| 4,850,342 A | 7/1989 | Hashiguchi et al. |

(Continued)

FOREIGN PATENT DOCUMENTS

CN    101669845    3/2010

OTHER PUBLICATIONS

International Search Report, PCT/US19/19207, dated May 14, 2019, 2 pgs.

(Continued)

*Primary Examiner* — Lynnsy M Summitt
(74) *Attorney, Agent, or Firm* — Jennings Strouss & Salmon PLC; Daniel R. Pote (57) ABSTRACT

Methods and apparatus for affixing a retaining washer proximate an interbody region following a direct lateral interbody fusion (DLIF) procedure. The system includes an installation device characterized by a width dimension W and a length dimension L; a retaining washer having a substantially planar surface region, the retaining washer configured to retain an interbody graft within an interbody region; and a screw having a shaft configured to secure the retaining washer to a vertebral body. The screw and the washer are configured to orient the screw shaft along an angle θ, where θ is a function of W and L.

9 Claims, 4 Drawing Sheets

(56) References Cited

U.S. PATENT DOCUMENTS

| | | | |
|---|---|---|---|
| 5,275,601 A * | 1/1994 | Gogolewski | A61B 17/8052 411/399 |
| 5,554,100 A | 9/1996 | Leiner et al. | |
| 5,569,183 A | 10/1996 | Kieturakis | |
| 5,601,553 A * | 2/1997 | Trebing | A61B 17/15 411/399 |
| 5,607,428 A * | 3/1997 | Lin | A61B 17/8047 606/287 |
| 6,127,597 A | 10/2000 | Beyar et al. | |
| 6,494,881 B1 | 12/2002 | Bales et al. | |
| 6,767,351 B2 * | 7/2004 | Orbay | A61B 17/68 606/287 |
| 6,893,444 B2 * | 5/2005 | Orbay | A61B 17/68 606/281 |
| 6,916,286 B2 | 7/2005 | Kazakevich | |
| 7,717,945 B2 * | 5/2010 | Jensen | A61B 17/1655 606/281 |
| 8,208,995 B2 | 6/2012 | Tearney et al. | |
| 8,391,571 B2 | 3/2013 | Cinquin et al. | |
| 8,409,080 B2 | 4/2013 | Gumbs et al. | |
| 8,556,985 B2 * | 10/2013 | Meridew | A61F 2/34 623/22.24 |
| 8,915,947 B2 * | 12/2014 | Robinson | A61B 17/7071 606/281 |
| 8,998,988 B2 * | 4/2015 | Phillips | A61B 17/7059 606/86 B |
| 9,060,808 B2 * | 6/2015 | Overes | A61B 17/68 |
| 9,107,708 B2 * | 8/2015 | Robinson | A61B 17/7071 |
| 9,301,785 B2 * | 4/2016 | Wallenstein | A61B 17/7059 |
| 9,687,142 B1 | 6/2017 | Lieberman et al. | |
| 2004/0024463 A1 | 2/2004 | Thomas, Jr. et al. | |
| 2004/0215196 A1 * | 10/2004 | Suddaby | A61B 17/1728 606/86 A |
| 2005/0187140 A1 | 8/2005 | Hunter et al. | |
| 2006/0147492 A1 | 7/2006 | Hunter et al. | |
| 2006/0195085 A1 * | 8/2006 | Happonen | A61B 17/8057 606/281 |
| 2006/0276793 A1 * | 12/2006 | Berry | A61B 17/8052 606/70 |
| 2007/0129719 A1 | 6/2007 | Kendale et al. | |
| 2009/0088604 A1 * | 4/2009 | Lowry | A61B 17/02 600/210 |
| 2009/0187072 A1 | 7/2009 | Manohara | |
| 2009/0204157 A1 * | 8/2009 | Fernandez Dell'Oca | A61B 17/1728 606/280 |
| 2009/0228048 A1 * | 9/2009 | Duncan | A61B 17/8061 606/286 |
| 2009/0292361 A1 | 11/2009 | Lopez | |
| 2009/0318968 A1 | 12/2009 | Duggal et al. | |
| 2010/0063590 A1 | 3/2010 | Cannistra | |
| 2010/0312286 A1 * | 12/2010 | Dell'Oca | A61B 17/8057 606/291 |
| 2010/0324364 A1 | 12/2010 | Sakaki | |
| 2012/0016192 A1 | 1/2012 | Jansen et al. | |
| 2012/0059470 A1 | 3/2012 | Weiman | |
| 2012/0078373 A1 * | 3/2012 | Gamache | A61B 17/8625 623/17.16 |
| 2012/0123206 A1 | 5/2012 | Vargas | |
| 2012/0130161 A1 | 5/2012 | Lauryssen | |
| 2013/0110183 A1 * | 5/2013 | Duggal | A61B 17/7064 606/328 |
| 2013/0312286 A1 * | 11/2013 | Fralin | A43B 3/242 36/101 |
| 2014/0194683 A1 | 7/2014 | Nakaguchi | |
| 2014/0236297 A1 | 8/2014 | Iott et al. | |
| 2014/0276015 A1 | 9/2014 | Whiseant | |
| 2015/0080973 A1 | 3/2015 | Eastlack et al. | |
| 2015/0257629 A1 | 9/2015 | Shanninain | |
| 2015/0289755 A1 | 10/2015 | Voros et al. | |
| 2015/0359575 A1 * | 12/2015 | Pech | A61B 17/8057 606/291 |
| 2016/0106551 A1 | 4/2016 | Grimberg et al. | |
| 2017/0112555 A1 * | 4/2017 | Wallenstein | A61B 17/7082 |
| 2017/0325852 A1 | 11/2017 | Chen et al. | |

OTHER PUBLICATIONS

Written Opinion, PCT/US19/19207, dated May 14, 2019, 4pgs.
EP Search Report, EP Application No. 17803535.8, dated May 24, 2019, 10pgs.
International Search Report, PCT/US17/62091, dated Feb. 5, 2018, 2pgs.
Written Opinion, PCT/US17/62091, dated Feb. 5, 2018, 8pgs.
International Preliminary Examination Report, PCT/US17/62091, dated May 2, 2018, 10 pgs.
International Search Report, PCT/US17/34341, dated Oct. 6, 2017, 6pgs.
Written Opinion, PCT/US17/34341, dated Oct. 6, 2017, 6pgs.

* cited by examiner

LOCKING SCREW ASSEMBLY FOR FACILITATING DIRECT LATERAL INTERBODY FUSION PROCEDURES

TECHNICAL FIELD

The present invention relates, generally, to methods and apparatus for facilitating a direct lateral interbody fusion (DLIF) procedure and, more particularly, to a screw locking mechanism for securing a prosthetic graft between vertebrae following disc removal.

BACKGROUND

Back pain frequently occurs in the facet joint between adjacent spinal vertebrae. The five facet joints on each side of the lumbar spine produce pain signals when they become arthritic or because of injury due to trauma, most typically at the L4/L5 and L5/S1 junctions.

Gaining clear access to the spine for both visualization and treatment is a critical aspect of spinal fusion surgery. Presently known spinal fusion procedures include: i) anterior lumbar interbody fusion (ALIF) which involves approaching the spine from the front of the body through an incision in the patient's abdomen; ii) posterior lumbar interbody fusion (PLIF) which involves approaching the spine through an incision in the patient's back over the vertebrae to be treated; iii) transforaminal lumbar interbody fusion (TLIF) which involves approaching the spine from the side through an incision in the patient's back; and iv) direct lateral interbody fusion (DLIF) which involves approaching the spine from the side through an incision in the patient's side or flank. Factors influencing which procedure to employ include the spinal condition to be treated, its location in the spinal column, surgical experience, available technology, and the patient's overall general health. Methods and apparatus for performing posterior lumbar interbody fusion (PLIF) procedures to relieve back pain are described in co-pending U.S. Ser. No. 15/353,428 filed Nov. 16, 2016, the entire contents of which are hereby incorporated herein by this reference.

In a typical DLIF procedure, on the other hand, the surgeon makes a small incision in the patient's side. A narrow passageway is formed through the underlying soft tissue while separating the psoas muscle fibers. This is also referred to as a transpsoas, or direct-lateral approach to interbody spinal fusion because it involves direct access through the psoas muscle rather than through the abdominal cavity or through a longer incision in the back.

During a DLIF procedure, the disc material between adjacent vertebrae is removed and replaced with a spacer (also referred to herein as an interbody graft) made of allograft bone and/or a synthetic material such as plastic or titanium. The interbody region surrounding the graft is packed with bone paste to allow the adjacent vertebral bodies to subsequently fuse together into a single, solid bone.

Presently known techniques for securing the graft within the space between the vertebrae following surgery include the SKYHAWK® Lateral Interbody Fusion System & Lateral Plate System available from Orthofix headquartered in Lewisville, Tex. However, existing retention systems are disadvantageous in that they do not allow the surgeon to orient the retention plate using the screw.

Methods and apparatus are thus needed which overcome the limitations of the prior art.

Various features and characteristics will also become apparent from the subsequent detailed description and the appended claims, taken in conjunction with the accompanying drawings and this background section.

BRIEF SUMMARY

Various embodiments of the present invention relate to methods and apparatus for, inter alia: i) a device for securing an interbody graft within the space between adjacent vertebrae following a direct lateral interbody fusion (DLIF) procedure or an anterior lumbar interbody fusion (ALIF) procedure; ii) a fastener assembly including an asymmetric washer having a major lobe and a minor lobe, and a screw configured to secure the major lobe proximate the interbody region to thereby retain the graft in place following a DLIF procedure; iii) a locking screw assembly including a washer and a screw having mating locking features configured to permit the surgeon to rotate the washer to a desired angular position relative to the interbody region; iv) a method for replacing disc material with an interbody graft in a DLIF procedure, inserting a washer and mating screw through a guide sleeve (also referred to as an installation tube) adjacent the interbody space, and thereafter attaching the screw to one (or both) of the vertebral bodies such that the washer restrains the graft in place during subsequent bony growth; v) a DLIF graft retention assembly including a dog bone washer secured to adjacent vertebrae by respective fasteners (e.g., screws); vi) a screw locking mechanism which allows the surgeon to selectively position a major lobe of a retaining washer proximate an interbody region using a drive tool through a guide sleeve; vii) a DLIF graft retention assembly including a locking washer and a screw having a screw head offset relative to the screw axis to thereby facilitate driving the screw into the vertebral body at an angle while disposing the screw head substantially coplanar with the vertebral body surface; viii) a DLIF graft retention assembly including a washer having a threaded through-hole disposed at an angle relative to the plane of the washer, and a headless screw configured to allow the surgeon to drive the screw into a vertebral body at an angle relative to the plane of the washer; and ix) a DLIF graft retention assembly including a locking washer and a screw having a screw head disposed at an angle relative to the screw shaft axis, where the washer is configured to resiliently deform as the screw is driven into the vertebral body.

It should be noted that the various inventions described herein, while illustrated in the context of a direct lateral interbody fusion (DLIF) procedure, are not so limited. Those skilled in the art will appreciate that the inventions described herein may contemplate any procedure in which it is desired to retain an interbody graft between adjacent anatomical surfaces.

Various other embodiments, aspects, and features are described in greater detail below.

BRIEF DESCRIPTION OF THE DRAWING FIGURES

Exemplary embodiments will hereinafter be described in conjunction with the following drawing figures, wherein like numerals denote like elements, and.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to devices and associated methods for performing surgical procedures, including but not limited to direct lateral interbody fusion (DLIF) procedures in which a spacer or insert such as an interbody graft is placed between anatomical structures (e.g., adjacent vertebrae).

By way of brief introduction, presently known DLIF procedures remove damaged disc material and insert an interbody graft packed with bone paste directly into the resulting space between vertebrae. However, following surgery, the graft may become dislodged form the disc space before sufficient bony growth occurs to permanently fuse the adjacent vertebrae into a single anatomical structure. Accordingly, the present invention provides a locking screw and washer configured to secure the graft into position until sufficient bony growth securely fuses the graft into place.

In an embodiment, a guide sleeve is inserted through the patient's side to permit access to the disc region. As explained in greater detail below, the ratio between the diameter and the length of the sleeve define the maximum angle at which a screw may be inserted into one of the vertebrae to secure a washer in place over the disc region, such that the graft remains constrained by the washer following surgery.

In an embodiment, the washer or retainer includes a major lobe (e.g. extending in the range of 12 millimeters from the through hole), a minor lobe (e.g. extending in the range of 3 millimeters from the through hole), and hex-shaped through hole configured to engage a corresponding hex region of the screw shaft. As the surgeon turns the screw into the vertebral body, the washer rotates until the minor lobe is positioned proximate the vertebral body, and the major lobe is positioned proximate the disc region. The surgeon can then rotate or counter-rotate the screw (and, hence, the washer) to optimally position the major lobe to prevent the graft from backing out.

The angle of the screw head relative to the screw shaft may be a function (e.g., the arc tangent) of the ratio of the diameter to the length of the installation tube.

Figure 1:
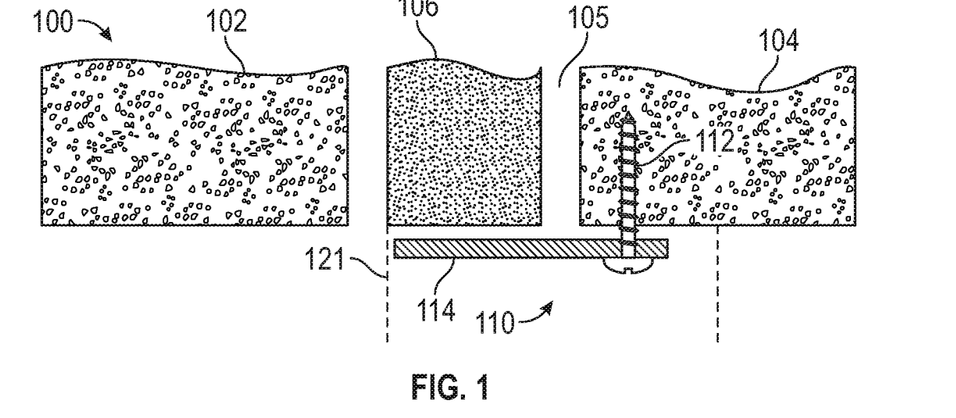
FIG. 1 is a schematic view of a first vertebral body, a second vertebral body, and a disc region disposed therebetween, where the disc material has been removed and replaced with an interbody graft in a direct lateral interbody fusion (DLIF) surgical procedure, depicting an interbody graft retention assembly including a screw and asymmetric washer configured to retain the interbody graft within the disc region in accordance with various embodiments.

Referring now to FIG. 1, a region of interest 100 includes a first vertebral body 102, a second vertebral body 104, and a disc region 105 disposed therebetween, where the disc material has been removed and replaced with an interbody graft 106 as the result of a direct lateral interbody fusion (DLIF) surgical procedure. An interbody graft retention assembly 110 includes a screw 112 and an asymmetric washer 114 configured to retain the interbody graft 106 within the disc region 105 following surgery. In an embodiment, a region of the screw shaft proximate the screw head may be configured to drivingly engage the washer, allowing the surgeon to optimally orient the washer over the interbody graft by turning the locked screw/washer assembly into position, as described in greater detail below. An installation tube or other access device 121 is schematically shown in dashed lines to generally indicate the available area within which the surgeon has to manipulate the interbody retention assembly during the procedure, as also described in greater detail below. (See, also, the generally analogous installation devices 221, 321, 421, 521, and 621 shown in FIGS. 2-6, respectively). The present invention contemplates device or techniques for providing access to the surgical site such as, for example, the QUADRx™ Lateral Retractor available from Orthofix.

Figure 2:
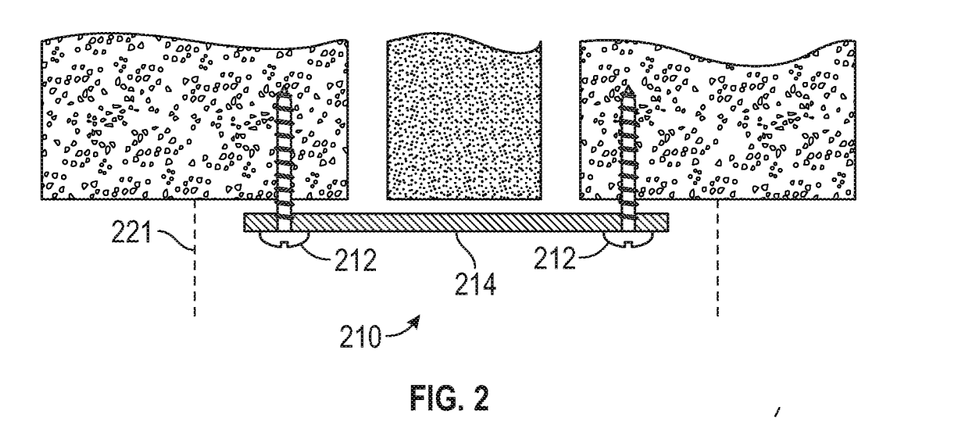
FIG. 2 is a schematic view of an alternate embodiment of an interbody graft retention assembly including a retaining bridge and a pair of fasteners configured to secure the bridge proximate the lateral region of the interbody space in accordance with various embodiments.

FIG. 2 depicts an alternate embodiment of an interbody graft retention assembly 210 generally analogous to that shown in FIG. 1, including a retaining bridge or plate 214 and a pair of fasteners (e.g., screws) 212 configured to attach the bridge to adjacent vertebrae while retaining the interbody graft within the interbody space. In this regard, the vertebrae are represented schematically in the drawing figures as flat surfaces; however, those skilled in the art will appreciate that the actual anatomical surfaces may be non-planar, and that the surgeon may remove portions of the vertebral surfaces to provide a substantially planar region for accommodating the retention plate, as desired. In various embodiments, one of the screws may be configured for interlocking engagement with the washer, such as, for example, using a hexagonal or other geometric configuration on the mating interface between an upper portion of the screw shaft (proximate the screw head) and the washer hole through which the screw extends.

Figure 3:
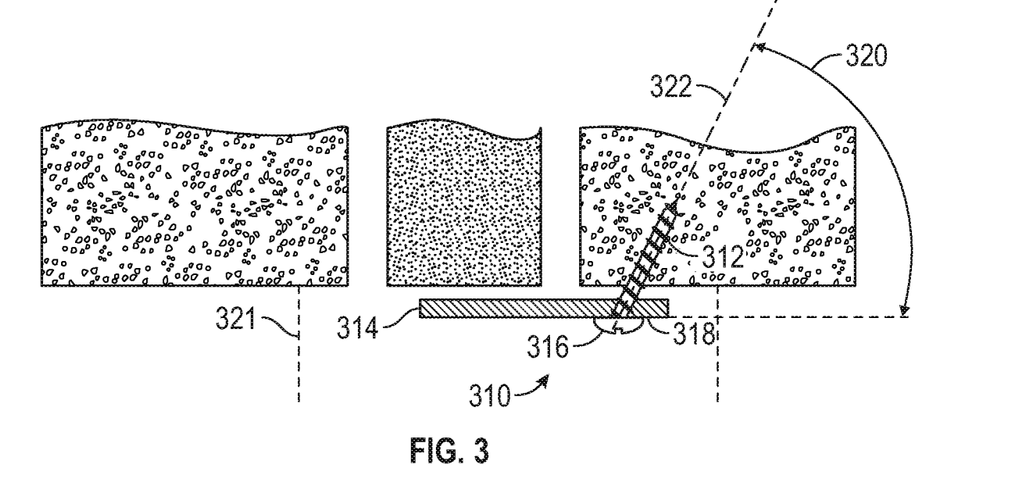
FIG. 3 is a schematic view of an alternate embodiment of an interbody graft retention assembly including an interlocking asymmetric washer and a screw having a screw head disposed at an angle relative to the screw shaft axis in accordance with various embodiments.

Turning now to FIG. 3, a further embodiment of an interbody graft retention assembly 310 includes an interlocking asymmetric washer and a corresponding interlocking screw 312 having a screw head 316 which includes a planar underside 318 disposed at an acute angle 320 relative to the screw shaft axis 322.

With continued reference to FIG. 3, the washer 314 may be constructed from a resiliently deformable material with sufficient strength to keep the graft contained, yet pliable enough to bend near the head 316 during tightening, and recover to permit the screw head to be positioned substantially flush (parallel) with the plane of the retention plate.

Figure 4:
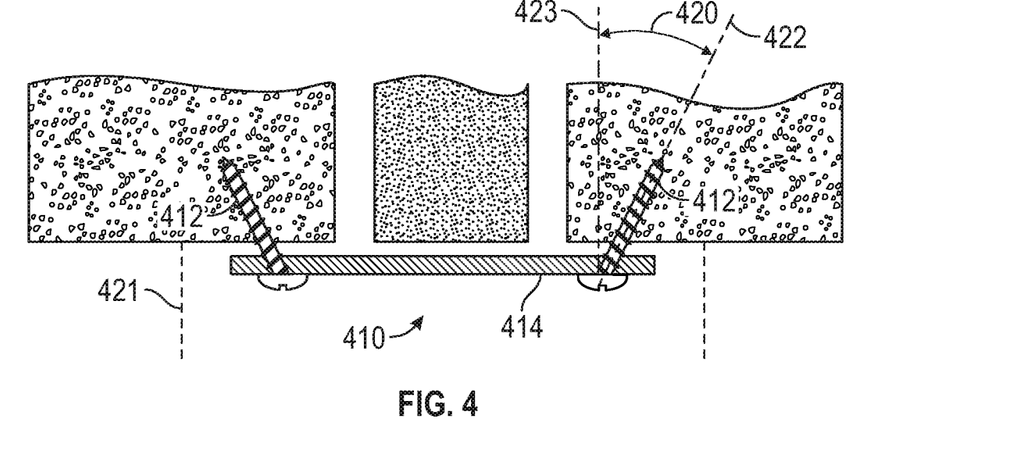
FIG. 4 is a schematic view of an alternate embodiment of an interbody graft retention assembly including a retaining bridge and a pair of fasteners configured to secure the bridge proximate the lateral region of the interbody space, where one or both of the screws includes a screw head disposed at an angle relative to its axis in accordance with various embodiments.

FIG. 4 is an alternate embodiment of an interbody graft retention assembly 410 including a retaining bridge (plate) 414 and a pair of fasteners 412 configured to secure the bridge proximate the lateral region of the interbody space, where one or both of the screws includes a screw head disposed at an angle relative to an axis perpendicular to a plane defining the underside of the screw head. In various embodiments, one of the screws may also be configured for interlocking engagement with the washer, as described above and further detailed below.

Figure 5:
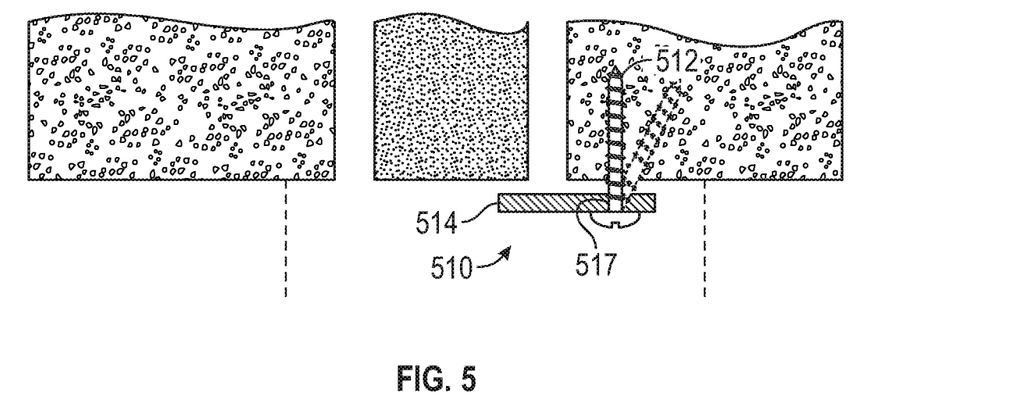
FIG. 5 is a schematic view of an alternate embodiment of an interbody graft retention assembly including a symmetric washer and a screw in accordance with various embodiments.

FIG. 5 is a further alternate embodiment of an interbody graft retention assembly 510 includes a substantially symmetric washer 514 and a screw 512. In the illustrated embodiment, the washer 514 includes a through-hole 517 which may be threaded, but which need not include a hex or other mechanical mechanism for locking with the washer, primarily because the rotational (angular) position of the washer is not critical to retaining the interbody graft; that is, the washer functions equally well regardless of it's angular position. The screw 512 may have a shaft which is substantially orthogonal to the underside 518 of the screw head (shown in solid lines); alternatively, the screw shaft may be disposed at an acute angle relative to the underside 518 of the screw head (shown in broken lines). In the case of an angles shaft, it may be advantageous to fabricate the washer and/or screw head using a deformable material (e.g., resiliently deformable) to allow the screw head/washer interface to compress as the screw is tightened into the vertebral body.

Figure 6:
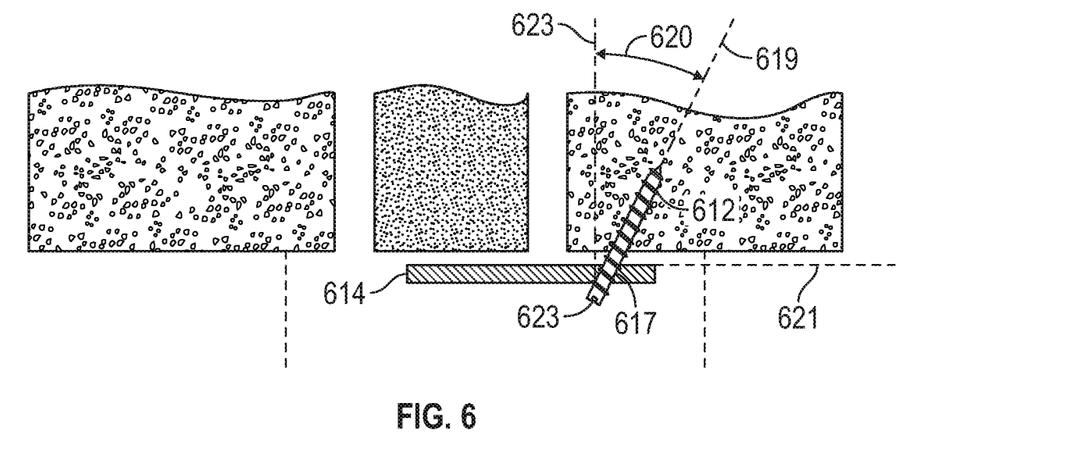
FIG. 6 is a schematic view of an alternate embodiment of a retention assembly including an optionally interlocking asymmetric washer and a headless screw, where the washer includes a threaded through-hole configured to guide the screw into the vertebral body at an inclined angle in accordance with various embodiments.

Referring now to FIG. 6, a further alternate embodiment of a retention assembly 610 includes an optionally interlocking asymmetric washer and a headless screw 612, where the washer includes a threaded through-hole 617 having a through-hole axis 619 configured to guide the screw into the vertebral body at an inclined angle 620 relative to a line 623 orthogonal to the surface 621 of the washer. In this way, the screw may be driven into the vertebral body at an angle without having a screw head interfere with the surface of the retaining plate (washer). Indeed, the headless screw may be screwed into place such that the entire distal end 623 (or a portion thereof) is disposed into the washer. The distal end 623 may embody one or more mechanical features configured to interface with a driving device (e.g., screw driver), as detailed below in conjunction with FIG. 10. In various embodiments the through-hole 617 may or not be threaded and/or include a hex or other mechanical feature configured to engage a corresponding locking portion of the screw shaft proximate the distal end 623 thereof.

Figure 7:
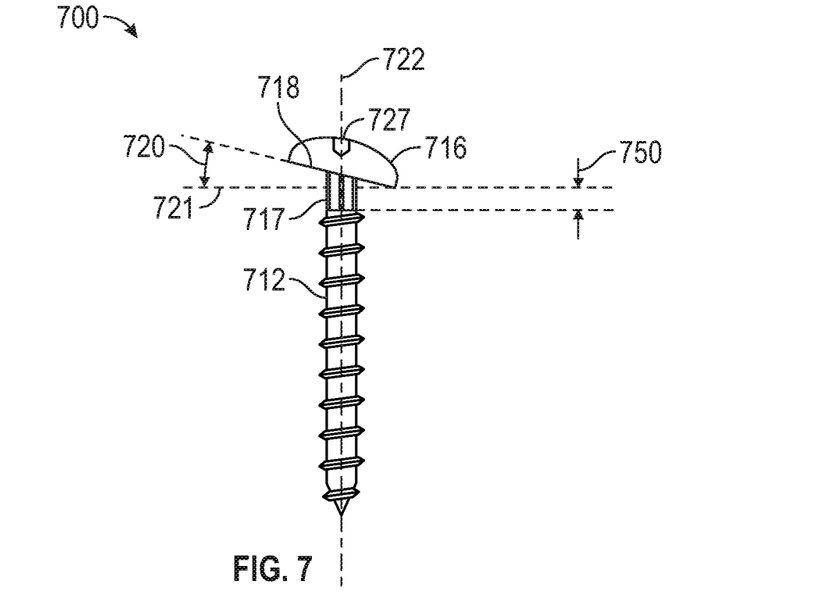
FIG. 7 is a front elevation view of an exemplary screw showing a locking feature and a screw head inclined at an acute angle relative to the screw head plane in accordance with various embodiments.

FIG. 7 depicts an exemplary screw 700 of the type which includes a head portion 716 having a substantially flat undersurface 718, inclined at an acute angle 725 relative to a plane 721 orthogonal to a centerline 722 of the screw shaft 712. The angle 725 may be in the range of 5 to 20 degrees, and preferably about 11.5 degrees. The shaft 712 includes an optional locking region 717 having a longitudinal extent 750 adjacent to or otherwise proximate the screw head. The dimension 750 may be in the range of 0.2 to 5 millimeters, and preferably about 2 mm. The locking feature 717 may comprise any mechanical configuration such as a hexagonal cross section which allows the screw to engage a washer such that the washer rotates along with the screw when so engaged. The head 716 includes a drive mechanism 727 (e.g., hex) for releasable driving engagement with a screw driver tool.

Figure 8:
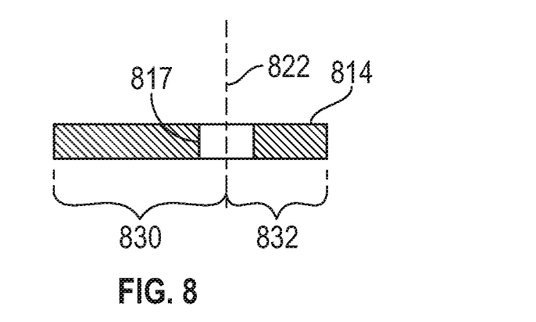
FIG. 8 is a top plan view of an exemplary asymmetrical washer depicting first and second lobes and an optional interlocking feature in accordance with various embodiments.

FIG. 8 is a top plan view of an exemplary asymmetrical washer 814 including a through-hole 817 which may optionally be threaded to accommodate corresponding screw threads, and which may also include an optional locking feature. For example, a first portion of the axial extent of the through-hole 817 may comprise a locking feature having a first effective cross section, and a second portion of the axial extent of the through-hole 817 may comprise mating screw threads having a second effective cross section smaller than the first cross section. In this way the screw shaft may be threaded along and through the through hole until the locking feature of the screw engages the locking feature of the washer, whereupon the washer is thereafter turned by the screw. In this context, the term asymmetrical suggests a first lobe or region 830 larger in size than a second lobe 832.

Figure 9:
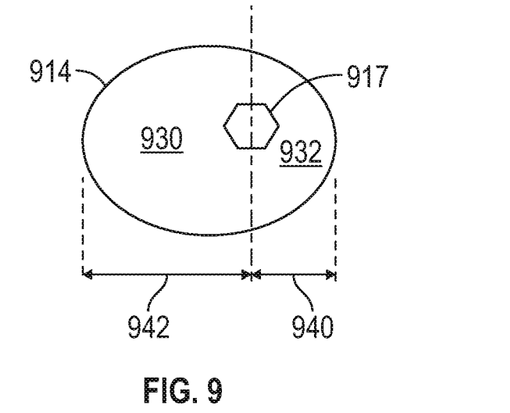
FIG. 9 is a top plan view of an exemplary dog bone type washer or bridge in accordance with various embodiments.

FIG. 9 is a top plan view of a washer or bridge 914 including a through-hole 917, a major lobe 930, and a minor lobe 932. In various embodiments, the major lobe 930 exhibits a major dimension 942 in the range of about 5 to 20 mm, and preferably about 8 to 14 millimeters, and most preferably about 10 to 12 mm. The minor lobe 932 exhibits a minor dimension 940 in the range of about 1 to 8 mm, and preferably about 2 to 4 millimeters, and most preferably about 3 mm. Alternatively, the dimension 942 may be approximately twice the length of dimension 940.

Figure 10:
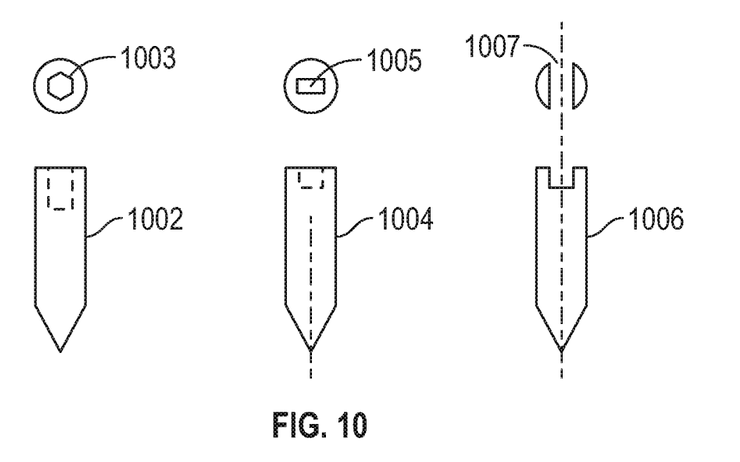
FIG. 10 depicts various exemplary headless screw configurations in accordance with various embodiments.

Referring again to FIG. 6 and also referring now to FIG. 10, various exemplary headless screw configurations include a first screw 1002 having a hex configuration 1003 inset into the top of the screw, a second screw 1004 having a rectangular configuration 1005 inset into the top of the screw, and a third screw 1006 having a keyway configuration 1007 extending across a top portion of the screw. Alternatively, the mechanical features for engaging a screw driver tool may take any form, and may extend out of (as opposed to into) the screw head, as desired.

Figure 11:
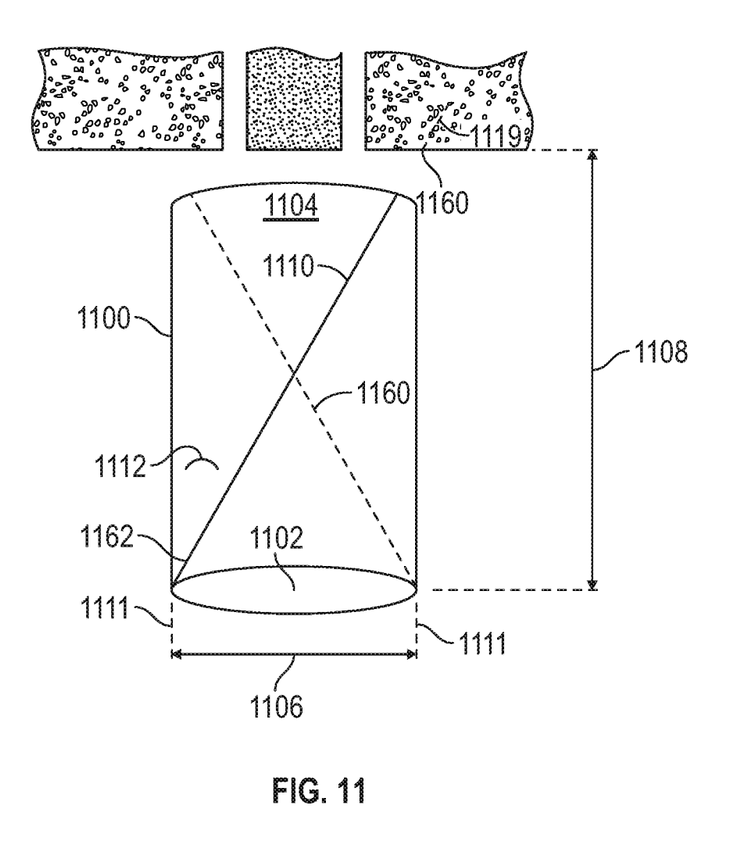
FIG. 11 is a schematic view of an exemplary guide sleeve illustrating design parameters for determining various geometric features of the foregoing components in accordance with various embodiments.

FIG. 11 is a schematic diagram of a guide sleeve, installation tube, lateral retractor, or other device 1100 used to provide access to the surgical site. In the illustrated embodiment, the device 100 is substantially cylindrical; however, those skilled in the art will appreciate that such devices may take any form and may be enclosed (including side walls), open (partial or no side walls), rectangular, or of any shape, size, and/or configuration designed to allow access to the anatomical site of interest. In addition, the access device may be structurally static, or dynamically expandable and retractable to define an access opening of a desired size and/or shape.

For present purposes, the installation tube may be characterized by a cross section (e.g., width or diameter) dimension 1106 and a length or depth dimension 1108, which together define an angle 1112 at which force may be applied to a driving tool (e.g., screw driver) along a drive line 1110 to thereby insert a screw into a vertebral body at position 1119. In the embodiment shown in FIG. 11, the installation "tube" has essentially the same width dimension 1106 at both a proximal end 1102 and a distal end 1104; however, those skilled in the art will appreciate that the width dimension may not be constant along the length of the device, and the distal end may exhibit a larger or smaller width dimension than the proximal end.

In various embodiments, the installation sleeve, tube, or retractor may exhibit an effective length (generally corresponding to the depth of penetration into the patient) in the range of about 50 to about 500 mm, and preferably about 75 to 125 mm, and most preferably about 100 mm. The width, or the effective diameter or working cross sectional dimension, may be in the range of 5 to 50 mm, and preferably about 10 to 30 mm, and most preferably about 20 mm.

Regardless of the particular configuration of the installation tube, for purposes of the present discussion one important metric surrounds the angle 1112 (relative to a line 1111 generally orthogonal to the "plane" of the surgical site) at which the surgeon may conveniently urge a driving tool along a drive line 1110. Angle 112 thus influences the design parameters associated with various geometric features of the foregoing components such as, for example, the angle of the through-hole relative to the plane of the retainer, and the angle of the screw head relative to the screw shaft.

With continued reference to FIG. 11, the size, shape, and configuration of the installation tube defines orientation of the drive line 1110 between a screw tip entry point 1160 and a drive point 1162 which corresponds to the proximal end of the drive tool manually manipulated by the surgeon. A similar drive line 1160 may be employed to drive a second screw (not shown) for dog bone and other retainer configurations where two or more screws are desired. Those skilled in the art will appreciate that one or more screws may also be driven into the vertebrae orthogonally (e.g., along a line substantially parallel to line 111), either in addition to or in lieu of driving one or more screws at the indicated angles.

Angle 1112 may be determined, in accordance with one embodiment, in accordance with the following relationship between the effective length dimension and the effective width dimension of the installation device:

$$\text{Tan}(\Theta)=[W/L]; \text{ and}$$

$$\Theta=\arctan[W/L]$$

Where $\Theta$=angle 1112; W=dimension 1106; L=dimension 1108; and arctan corresponds to the inverse tangent function, also expressed as $\text{Tan}^{-1}$.

By way of non-limiting example, for an installation device having a nominal working length of 100 mm and a nominal working width of 20 mm, the driving toll and screw shaft would be driven along line 1110 at an angle 1112 in the range of 2 to 20 degrees, and preferably about 5 to 15 degrees, and in this particular example about 11.3 degrees;

$$\text{where } \Theta=\arctan[20/100]=\text{Arc Tan}[0.2]=11.3°.$$

Accordingly, angles 420 and 720 illustrated in FIGS. 4 and 7, respectively, may similarly be determined in accordance with the effective length and width dimensions of the installation apparatus. Moreover, the angle of the through-hole 617 along line 619 relative to line 623 (orthogonal to the plane of the retainer) as well as angle 620, in the embodiment shown in FIG. 6 may also be determined in accordance with the foregoing design metrics.

By way of non-limiting example, a screw for use in a direct lateral interbody fusion procedure may include a screw shaft and a screw head, where the shaft axis is formed at an angle θ relative to a plane orthogonal to the underside of the head. The angle θ may be determined as a function of a cross section dimension and a depth dimension associated with the access apparatus (e.g., installation tube). The screw may be driven into a vertebral body or other anatomical site along the screw axis, such that the underside of the head is oriented substantially parallel to a washer or plate used to retain an interbody graft. If desired, a linear region along the screw shaft proximate the head may include a locking mechanism configured to engage a corresponding through-hole in the washer, to allow the surgeon to secure the washer at a desired angular orientation, for example, to dispose a major lobe of the washer over the interbody graft region of the surgical site.

In an alternate embodiment, a headless screw may be employed in conjunction with a washer having a through-hole disposed at an angle θ relative to an axis orthogonal to a plane of the washer. In this way, the surgeon may drive the screw into the anatomical site without interference between a screw head and the washer during installation.

A surgical assembly is thus provided for affixing a retaining washer proximate an interbody region following a direct lateral interbody fusion (DLIF) procedure. In an embodiment the assembly includes: an installation device characterized by a width dimension W and a length dimension L; a retaining washer having a substantially planar surface region, the retaining washer configured to retain an interbody graft within an interbody region; and a screw having a shaft configured to secure the retaining washer to a vertebral body; wherein the screw and the washer are configured to orient the screw shaft along an angle θ, where θ is a function of W and L.

In various embodiments, θ may be proportional to the ratio [W/L], proportional to the arctangent of [W/L], or equal to the arctangent of [W/L].

In an embodiment the screw comprises a head having a substantially flat underside, and further wherein the screw shaft is oriented at angle θ relative to a line orthogonal to the flat underside of the screw head.

In an embodiment the screw shaft comprises a first locking mechanism extending along a portion of the shaft proximate the head, and the washer comprises a second locking mechanism configured to engage the first locking mechanism.

In an embodiment the proximal portion of the shaft comprising the locking mechanism is in the range of about 0.2 to 5 millimeters, and preferably about 2 mm.

In an embodiment the first and second locking mechanisms comprise mating geometric configurations.

In an embodiment the washer comprises a major lobe and a minor lobe, and the first and second locking mechanisms are configured to permit the surgeon to orient the major lobe proximate the interbody region by rotating the screw to a desired angular position.

In an embodiment the washer comprises a through-hole oriented at angle θ relative to a line orthogonal to the flat underside of the screw head.

In an embodiment the screw shaft and the through-hole are configured for mating threaded engagement.

In an embodiment the washer comprises a through-hole oriented at angle θ relative to a line orthogonal to the substantially planar surface region of the washer.

In an embodiment the screw is substantially headless.

In an embodiment the screw and the through-hole are configured for mating threaded engagement.

In an embodiment the screw shaft comprises a first locking mechanism extending along a proximal portion of the shaft, and the washer comprises a second locking mechanism configured to engage the first locking mechanism.

In an embodiment the washer comprises a major lobe, and further wherein the first and second locking mechanisms are configured to permit manual orientation of the major lobe proximate the interbody region.

A locking screw and washer assembly is thus provided for use with an installation device in a direct lateral interbody fusion (DLIF) procedure, where the installation device is characterized by a width dimension W and a length dimension L. in various embodiments the assembly includes: a retention plate configured to retain an interbody graft within an interbody region following the DLIF procedure, the retention plate comprising a major lobe, a substantially co-planar minor lobe, and a through-hole disposed therebetween, the through-hole disposed at an angle θ relative to a line orthogonal to the plane within which the major and minor lobes lie; and a screw having a head with a flat underside and a shaft, wherein the shaft is oriented at a fixed angle θ relative to the flat underside of the screw head; wherein θ is proportional to the arctangent of [W/L].

In an embodiment the screw shaft comprises a first locking mechanism extending along a proximal portion of the shaft; the retention plate comprises a second locking mechanism configured to engage the first locking mechanism; and the first and second locking mechanisms are configured to permit manual orientation of the major lobe at a desired angular position at the surgical site.

A method is also provided for installing a major lobe of a retaining plate between adjacent boney anatomical structures during a surgical procedure. The method includes: placing an installation tube adjacent the surgical site, the installation tube being characterized by a width dimension W, a length dimension L, and an insertion angle θ which is proportional to the arctangent of the quantity [W/L]; placing the retaining plate adjacent one of the boney anatomical structures; inserting a screw into a through-hole of the retaining plate, wherein the through-hole is inclined at an angle θ relative to a line orthogonal to the plane of the retaining plate; and rotating the screw along its axis to simultaneously: i) secure the screw to one of the boney anatomical structures; and ii) orient the major lobe of the retaining plate between the adjacent boney anatomical structures.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A surgical assembly for affixing a retaining washer proximate an interbody region following a direct lateral interbody fusion (DLIF) procedure, the assembly comprising:
    an installation device characterized by a width dimension W and a length dimension L;
    a retaining washer having a substantially planar surface region, the retaining washer configured to retain an interbody graft within an interbody region; and
    a screw having a shaft configured to secure the retaining washer to a vertebral body;
    wherein:
    the screw and the washer are configured to orient the screw shaft along an angle θ, where θ is a function of W and L;
    the screw comprises a head having a substantially flat underside;
    the screw shaft is oriented at angle θ relative to a line orthogonal to the substantially flat underside of the screw head; and
    the screw shaft comprises a first locking mechanism extending along a portion of the shaft proximate the head, and the washer comprises a second locking mechanism configured to engage the first locking mechanism.

2. The assembly of claim 1, wherein a proximal portion of the shaft is in the range of about 0.2 to 5 millimeters.

3. The assembly of claim 2, wherein the first and second locking mechanisms comprise mating geometric configurations.

4. The assembly of claim 1, wherein a proximal portion of the shaft is in the range of about 2 mm.

5. The assembly of claim 1, wherein the retaining washer comprises a major lobe and a minor lobe, and further wherein the first and second locking mechanisms are configured to permit the surgeon to orient the major lobe proximate the interbody region by rotating the screw to a desired angular position.

6. The assembly of claim 1, wherein the retaining washer comprises a through-hole oriented at angle θ relative to the line orthogonal to the substantially flat underside of the screw head.

7. The assembly of claim 6, wherein the screw shaft and the through-hole are configured for mating threaded engagement.

8. The assembly of claim 1, wherein the washer comprises a through-hole oriented at angle θ relative to the line orthogonal to the substantially planar surface region of the washer.

9. A method of installing a major lobe of a retaining plate between adjacent boney anatomical structures during a surgical procedure, the method comprising:
    placing an installation tube adjacent a surgical site, the installation tube being characterized by a width dimension W, a length dimension L, and an insertion angle θ which is proportional to the arctangent of the quantity [W/L];
    placing the retaining plate adjacent one of the boney anatomical structures;
    introducing a screw and a distal end of a drive tool into the installation tube;
    inserting the screw into a through-hole of the retaining plate, wherein the through-hole is inclined at the angle θ relative to a line orthogonal to the plane of the retaining plate; and
    rotating the screw along its axis to simultaneously: i) secure the screw to one of the boney anatomical structures; and ii) orient a major lobe of the retaining plate between the adjacent boney anatomical structures.

\* \* \* \* \*